(12) United States Patent
Neuwirth (10) Patent No.: US 7,875,297 B2
(45) Date of Patent: Jan. 25, 2011

(54) METHOD FOR TREATING MENORRHAGIA

(75) Inventor: Robert S. Neuwirth, Englewood, NJ (US)

(73) Assignee: Ablation Products LLC, Englewood, NJ (US)

( * ) Notice: Subject to any disclaimer, the term of this patent is extended or adjusted under 35 U.S.C. 154(b) by 139 days.

(21) Appl. No.: 12/231,340

(22) Filed: Sep. 2, 2008

(65) Prior Publication Data

US 2009/0068284 A1     Mar. 12, 2009

Related U.S. Application Data

(62) Division of application No. 10/825,930, filed on Apr. 16, 2004, now Pat. No. 7,419,687.

(60) Provisional application No. 60/463,255, filed on Apr. 16, 2003.

(51) Int. Cl.
    *A61K 33/38*     (2006.01)
    *A61K 33/00*     (2006.01)
    *A01N 59/16*     (2006.01)
    *A01N 59/00*     (2006.01)

(52) U.S. Cl. ........................................ 424/618; 424/718

(58) Field of Classification Search ........................ None
See application file for complete search history.

(56) References Cited

U.S. PATENT DOCUMENTS 3,930,000 A * 12/1975 Margraf ...................... 514/184
5,073,365 A * 12/1991 Katz et al. ................... 427/2.24
5,891,457 A * 4/1999 Neuwirth ..................... 424/430
6,187,346 B1 * 2/2001 Neuwirth ..................... 424/618

OTHER PUBLICATIONS

Solubility Table [online] retrieved from http://en.wikipedia.org/wiki/solubility_table on Aug. 20, 2007; 4 pages.*

* cited by examiner

*Primary Examiner*—Ernst V Arnold
(74) *Attorney, Agent, or Firm*—Olson & Cepuritis, Ltd.

(57) ABSTRACT

A delivery vehicle for a silver ion source such as silver nitrate and the like, suitable for use in the treatment of menorrhagia, comprises a plurality of physiologically inert beads bearing a tissue cauterizing amount of a silver ion source. Preferably the beads are made of a physiologically inert polymer, ceramic or stainless steel. The silver ion source preferably is silver nitrate and can be substantially pure silver nitrate, or can comprise silver nitrate in combination with a physiologically tolerable binder or a diluent. Suitable binders include physiologically tolerable synthetic polymeric binders, polysaccharide binders, and the like. Diluents can include other salt materials such as potassium nitrate. The beads are useful in treating menorrhagia of a mammalian uterus. The beads can be delivered to the uterus via a catheter, and are distributed throughout the uterine cavity by uterine massage or like expedient. Silver ions are delivered to the endometrium and cause necrosis of the endometrial tissue. The silver ions remaining within the uterine cavity can then be neutralized with a sodium chloride solution delivered to the uterus e.g., by catheter, and the beads recovered from the uterus.

3 Claims, 5 Drawing Sheets

METHOD FOR TREATING MENORRHAGIA

CROSS REFERENCE TO RELATED APPLICATION

This application is a division of U.S. patent application Ser. No. 10/825,930, filed Apr. 16, 2004, now U.S. Pat. No. 7,419,687, which claims benefit of U.S. Provisional Patent Application No. 60/463,255, filed Apr. 16, 2003.

FIELD OF THE INVENTION

This invention relates generally to vehicles for delivering tissue necrosing agents. More specifically, the invention relates to inert beads having a silver ion releasing compound such as silver nitrate deposited thereon, and suitable for delivering a tissue cauterizing amount of silver ions to the endometrium of a mammalian uterus for the treatment of menorrhagia.

BACKGROUND OF THE INVENTION

Apparatus and methods for necrosing of the endometrium of a mammalian uterus, useful in treating excessive bleeding (menorrhagia) sterilization procedures, and cancer treatments, are known in the art. Thermal and cryogenic treatments have been utilized in such necrosing techniques and typically involve either the direct or indirect application of heat or cold to the tissue to be treated.

In addition to thermal and cryogenic treatments, methods involving application of caustic chemicals within the human body to treat menorrhagia, achieve sterilization and treat cancers also are known. The use of caustic chemicals as locally destructive agents has been attempted but has been limited by concerns about safety and control of the delivery of various agents as well as other shortcomings due to the methods of application, e.g., blind placement of a particular solid chemical. For example, as described by Babcock, W., *Chemical Hysterectomy*, Jnl. Obstet. & Gyn., Vol. 7, p. 693 (1924), application of gauze strips soaked in a saturated solution of zinc chloride to the uterine walls has reportedly been used to induce amenorrhea, to cause sterility, and to treat tumors. However this procedure has several disadvantages. The application of the gauze strips is a blind procedure, however. The zinc chloride soaked gauze is packed in the uterus until the practitioner feels the cavity is full. The strips are left in place for a predetermined length of time and then removed. Delivery to and removal from the uterine cavity of the caustic gauze strips necessarily entails substantial risk of infection and of contacting the vaginal walls wherein the caustic could damage the vaginal and other tissue that are not the target of the treatment. Accordingly, successful use of this methodology requires substantial skill and experience, limiting the availability of the procedure to women with access to highly trained medical personnel.

Use of caustic agents such as silver nitrate, zinc chloride and copper sulfate has been studied for use in chemical sterilization by chemically cauterizing the fallopian tubes. However, as discussed by Richart, R., *Female Transcervical Sterilization*, Chapter 3, Harper & Row (1983), even when massive tubal necrosis was achieved with the application of silver nitrate, a significant proportion of fallopian tubes remained open. When compositions for the sustained release of the caustic agents were employed it was found that control over the release of the caustic agents was insufficient to avoid unacceptable side effects. Additionally, use of strong caustic agents such as acids and alkalies would require the concomitant use of equally strong neutralizing agents whose use is also laden with risk. Use of such agents also puts the practitioner in the difficult position of titrating the neutralization of the caustic agent in the patient's uterus and Fallopian tubes.

Neuwirth describes a particularly effective method for treating menorrhagia, which involves administering a silver nitrate-containing paste to the uterine cavity and distributing the paste therein. See, e.g., U.S. Pat. No. 6,197,351; U.S. Pat. No. 6,187,346; U.S. Pat. No. 6,165,492; and U.S. Pat. No. 5,891,457; the relevant disclosures of which are incorporated herein by reference. The silver nitrate causes necrosis of the endometrium, which in turn stops excess uterine bleeding associated with menorrhagia. After treatment, the caustic silver nitrate is effectively neutralized by administering a solution of sodium chloride, usually physiologic saline, to the uterine cavity. Sodium chloride reacts with the silver nitrate to form insoluble (non-caustic) silver chloride. The silver chloride is then flushed out of the uterus along with any loose necrosed tissued present in the uterus.

Delivery of silver nitrate as a paste, as described by Neuwirth, requires some degree of care to ensure that the paste does not come into prolonged contact with tissues that are not in need of cauterization such as the Fallopian tubes. There exists, therefore, a need for improved vehicles for a more precise delivery of silver nitrate to the uterine cavity to implement chemical cauterization of the endometrium. The present invention provides such improved delivery vehicles.

SUMMARY OF THE INVENTION

A delivery vehicle for a silver ion releasing compound such as silver nitrate suitable for tissue necrosis, e.g., for use in the treatment of menorrhagia, comprises a plurality of physiologically inert beads bearing a tissue necrosing amount of a solid silver ion releasing composition. The beads can be composed of any physiologically inert material such as a polymer, a ceramic or stainless steel. The solid silver ion releasing composition can be a water-soluble inorganic silver salt, a water-soluble organic silver salt, and the like water-soluble oxidizing agent. A preferred water soluble inorganic silver salt is silver nitrate, which can be administered as substantially pure silver nitrate, as silver nitrate in combination with a physiologically tolerable binder or a diluent. A preferred water-soluble organic silver salt is silver acetate, and the like, alone or in combination with a physiologically tolerable binder or diluent. Suitable binders include physiologically tolerable synthetic polymeric binders, polysaccharide binders, and the like. Diluents can include other water soluble salts such as potassium nitrate, and the like.

The beads are preferably substantially spherical in shape and have an average diameter in the range of about 1 to about 6 millimeters, more preferably about 2 to about 4 millimeters. Preferably the beads are substantially uniform in size.

Preferably each bead carries a composition containing at least about 20 milligrams, more preferably about 50 milligrams to about 150 milligrams of a silver ion releasing compound such as silver nitrate, silver acetate, and the like, per bead.

The beads carrying a silver ion releasing composition are useful in treating menorrhagia of a mammalian uterus. The beads are delivered to the uterus via a catheter, and are distributed throughout the uterine cavity by uterine massage or like manipulation. Silver ions are delivered to the endometrium and cause necrosis of the endometrial tissue as well as some of the myometrium. The silver ions remaining within the uterine cavity can thereafter be neutralized, usually with a sodium chloride solution delivered to the uterus by catheter. Thereafter the beads are recovered from the uterus, for example, by suction, by flushing, by mechanical removal, or the like expedient.

DETAILED DESCRIPTION OF PREFERRED EMBODIMENTS

As used herein, the term "necrosis" and grammatical variations thereof means death of cells in a tissue. The term "chemical necrosis" and grammatical variations thereof means necrosis resulting from contact with a caustic chemical agent. The terms "physiologically inert" and "physiologically tolerable" as used herein and in the appended claims in references to materials or chemical components of the delivery vehicles of the present invention mean that the material or chemical component does not produce an adverse physiological reaction to the patient when present in the uterine cavity of the patient. Adverse physiological reactions include, for example, allergic and other systemic reactions, local inflammation not attributable to the silver nitrate, and the like.

The present invention provides a vehicle suitable for delivering a silver ion source such as silver nitrate and the like to the uterine cavity of a patient suffering from menorrhagia to chemically necrose the endometrium. The delivery vehicle comprises a plurality of physiologically inert beads bearing a solid silver ion source. The solid silver ion source adheres firmly to the beads, but the beads readily release a silver ion bearing composition when the beads come into contact with the moist endometrium of the uterus. The solid silver ion source can be coated on the external surface of a bead, or can be present at least partially within a porous bead.

Preferably the beads are substantially spherical in shape and have an average diameter in the range of about 1 to about 6 millimeters, more preferably about 2 to about 4 millimeters.

The beads can be made of any physiologically inert material which can meet governmental regulatory requirements, such as United States Food and Drug Administration requirements for medical devices received within the uterine cavity. The bead can be composed of a physiologically inert polymer such as polystyrene, polyethylene, polypropylene, nylon, polyethyleneterephthalate (PET), polyurethane, ethylene/vinyl acetate copolymers, and the like. Alternatively the beads can be made of a physiologically inert ceramic or of stainless steel. The beads can be perforated, spongiform, porous, or non-porous. Porous beads can be polymeric foam beads, such as polypropylene foam or polyethylene foam beads, or can be beads having machined pores or perforations, molded pores, and the like. Preferably the beads are nylon, polystyrene or polypropylene beads, more preferably having a specific gravity of less than 1 so that the beads can be readily removed from the uterine cavity after treatment by flushing with a saline solution or like expedient. Perforations or grooves in the beads, when present, can increase the loading of a silver ion releasing compound, such as silver nitrate, carried by the beads. For example, the beads can include one or more through perforations which can be filled with a silver ion releasing composition. Alternatively, the beads can have cavities or pits in the surface of the beads to hold additional silver ion source therein. Reticulated polyurethane beads are also suitable.

The silver ion delivery vehicles of the present invention can be manufactured by a variety of methods known in the art. For example, the beads can be coated with a molten silver nitrate composition, such as substantially pure silver nitrate, or a mixture of silver nitrate and up to about 25 weight percent of a diluent such as potassium nitrate, preferably no more than about 20 weight percent potassium nitrate, more preferably no more than about 5 percent by weight potassium nitrate. The molten silver nitrate composition can be deposited on the beads by spraying, for example, by spraying a molten silver nitrate composition onto a fluidized bed of beads. The beads also can be coated by combining the beads with a molten silver nitrate composition in a rotating kiln, a pin blender, and the like. Pure silver nitrate melts at a temperature of about 212° C. When a molten silver nitrate composition is deposited on a bead, preferably the bead has a softening temperature or a melting point above the melting point of the silver nitrate composition.

Alternatively, an aqueous composition containing a silver ion source such as a water-soluble inorganic silver salt, e.g., silver nitrate, silver sulfate, silver perchlorate, silver permanganate, and the like, or a water soluble organic silver salt, e.g., silver acetate, silver lactate monohydrate, and the like, together with a binder can be deposited on the beads and dried to provide silver ion delivery vehicles of the present invention. The aqueous composition can be a paste or a fluid containing a thickening binder (e.g., a dextran and the like), such as are described in U.S. Pat. No. 6,197,351 to Neuwirth, the relevant disclosures of which are incorporated herein by reference. Other suitable binders include any physiologically tolerable binder, such as synthetic polymeric binders and thickeners (e.g., poloxamer polymers, carbomer polymers, polyvinylpyrrolidone, and the like), gelatin, hardened gelatin, polysaccharides (e.g., dextrans, microcrystalline cellulose, methylcellulose, xanthan gum, guar, gum, and the like), and like thickening and binding agents, so long as they are of a grade suitable for use in intrauterine preparations. Pharmaceutically acceptable binders, carriers, diluents, disintegrants, and the like are described in *Remington's Pharmaceutical Sciences,* 14th Ed., Mack Publishing Co., pp. 1650-1653 (1970), the relevant disclosures of which are incorporated herein by reference to the extent pertinent.

In one preferred coating method, the silver nitrate-containing composition can be an aqueous composition comprising silver nitrate and a polymeric binder such as polyvinylpyrrolidone, and the like. The composition can be applied to the beads in any suitable manner. Preferably, the composition is applied as a uniform coating having a relatively smooth surface structure and a relatively constant thickness. For example, the composition may be applied to the beads by utilizing a pneumatic spray gun, by dipping, and the like expedients. Ideally, spraying is continuous, with substantially concurrent drying so that the beads do not become too moist (overly wet) and stick together. The freshly sprayed silver nitrate coating is dried as quickly as possible to avoid agglomeration of the beads. Other suitable methods include the use of fluidized-bed processes to coat the beads with a silver nitrate composition. Modified coating drums (e.g., cylindrical horizontally rotating units with a perforated wall) are also suitable for coating the beads with silver nitrate.

In another preferred embodiment, solid silver nitrate, as a powder or as fine crystals, can be added as a filler to a polymer melt, optionally with a blowing agent, during the bead-making process. Beads of silver nitrate filled polymer can then be extruded to form a silver nitrate delivery vehicle comprising a porous bead with silver nitrate dispersed therein. Preferably the bead is water swellable or water permeable, so that silver nitrate in the interior of the bead can be released when the beads are in contact with the endometrium in the uterus. Alternatively, an aqueous silver nitrate solution can be imbibed into a preformed, porous, water swellable or water permeable polymer bead.

Figure 1:
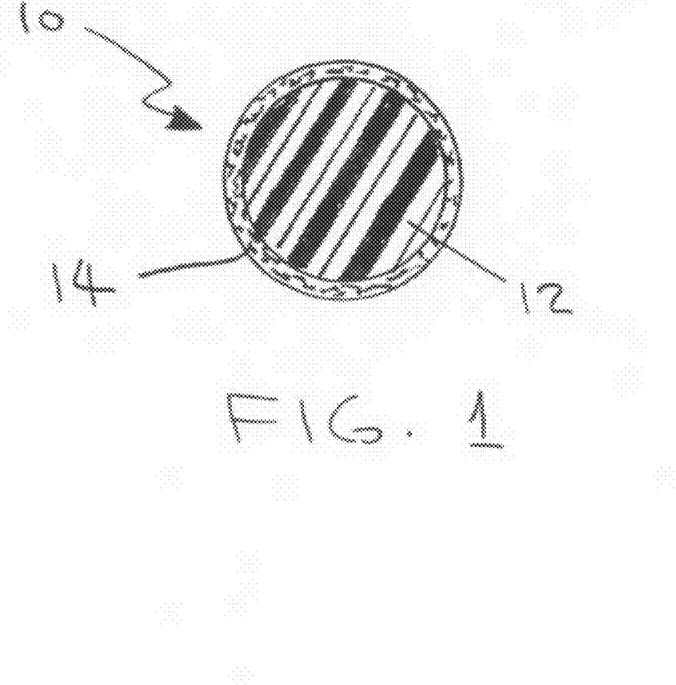
FIG. 1 is a cross-sectional view of a bead having a silver nitrate-containing composition coated on the exterior surface of the bead.
Figure 2:
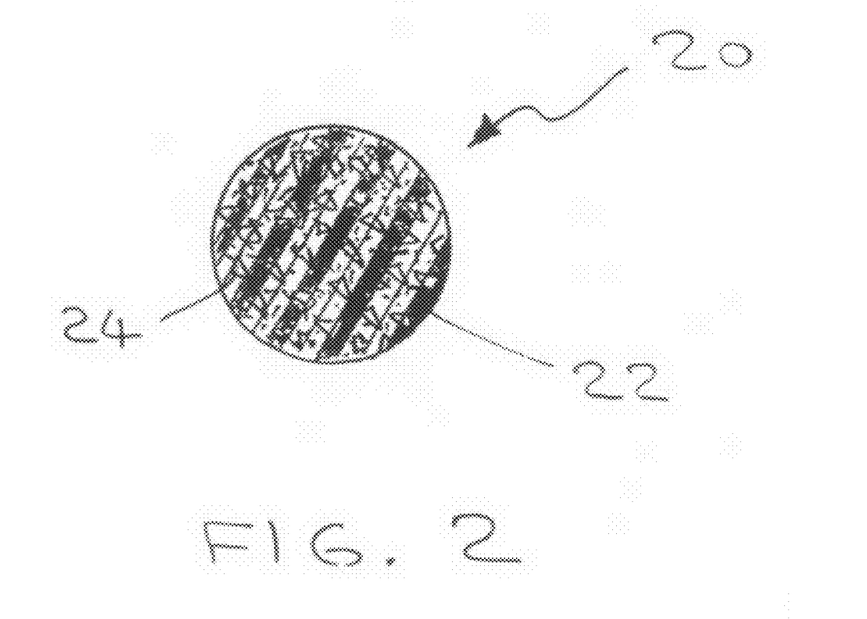
FIG. 2 is a cross-sectional view of a porous bead having a silver nitrate-containing composition deposited within the pores of the bead.

FIG. 1 is a cross-sectional view of a silver nitrate delivery vehicle 10, comprising a polymeric bead 12, such as a polypropylene or polystyrene bead, having a layer 14 of silver nitrate dispersed in polyvinylpyrrolidone deposited on the surface of bead 12. FIG. 2 is a cross-sectional view of a silver nitrate delivery vehicle 20 comprising a porous polymeric bead 22 having silver nitrate 24 within the pores of bead 22.

Porous beads preferably have an open cell structure and are composed of a hydrophilic polymer which is water permeable such as nylon or polyurethane, for example, or have surfaces that are hydrophilic.

Blowing agents that can be used to form porous polymeric materials are well known in the art. Suitable blowing agents and methods of manufacturing foamed polymeric materials are described in Frados, *Plastics Engineering Handbook of the Society of Plastics Industry, Inc.*, Chapter 20, Van Nostrand Reinhold Co., New York, pp. 499-599 (1976). Suitable blowing agents include, for example, chemical blowing agents such as azobisisobutyronitrile, azodicarbonamide, and the like; and gases such as carbon dioxide, nitrogen, and the like.

The plurality of beads delivered to the uterus includes a sufficient quantity of silver ions to produce the level of endometrial necrosis desired by the clinician performing the treatment. The released silver ions ($Ag^+$) react in the cells with moieties such as proteins, sulfides, chlorides, and the like that are vital to cell metabolism and thus initiate necrosis. Preferably a sufficient number of beads is administered to the uterine cavity to provide a total quantity of silver ions in the range of about 25 $mg/cm^2$ to about 150 $mg/cm^2$ of endometrium, preferably about 50 $mg/cm^2$ to about 100 $mg/cm^2$ of endometrium.

For a human uterine cavity of normal size, preferably about 15 to about 25 silver ion bearing beads having an outside diameter of about 2 to about 4 millimeters are introduced at one time. More preferably about 20 such beads are introduced into the uterine cavity at a time.

In the case of silver nitrate, preferably each bead can release an amount of silver nitrate in the range of about 20 to about 150 milligrams, more preferably about 50 to about 150 milligrams.

Another aspect of the present invention is a method of treating menorrhagia comprising the steps of administering to the uterine cavity of a patient suffering from menorrhagia a plurality of physiologically inert beads bearing a tissue cauterizing amount of a solid silver ion source such as silver nitrate and the like; massaging the uterus to distribute the beads therein; maintaining the beads in contact with the endometrial lining of the uterus for a time period sufficient to necrose the endometrial tissue; flushing the uterine cavity with an aqueous saline solution to neutralize the silver ions present in the uterine cavity; and recovering the beads from the patient's uterus in any convenient manner.

The present invention is illustrated by the following examples.

Example 1

Preparation of $AgNO_3$ Bearing Beads

A. Preparation of Coating Solutions

Coating Solution A was prepared by dissolving about 1 gram of silver nitrate in about 4 milliliters of water and adding thereto a solution of about 0.4 grams of polyvinylpyrrolidone (K-120) in about 4 milliliters of water.

Coating Solution B was prepared by adding about 4 milliliters of 70% denatured ethanol to about 8 milliliters of Coating Solution A.

B. Coating of Beads (i) Polypropylene beads having a diameter of about 3 millimeters and perforated polystyrene beads having a diameter of about 5 millimeters were soaked in Coating Solution A for about 2 minutes, removed from the coating solution, and were dried at ambient room temperature for about 30 minutes. The perforated polystyrene beads had single, substantially cylindrical through perforation having a diameter of about 1 millimeter in each bead.

(ii) Polypropylene and polystyrene beads as described in (i) above were soaked in Coating Solution B for about 2 minutes, removed from the coating solution, and were dried at ambient room temperature for about 30 minutes.

(iii) The surfaces of polypropylene and perforated polystyrene beads as described in (i) above were roughened and the beads were then coated with Coating Solution A as described in (i) above. The surface of each bead was roughened by rolling the bead under a file using a circular oscillating motion (about 25 oscillations) followed rolling the bead under an emery board using a circular oscillating motion (about 50 oscillations).

(iv) Surface roughened polypropylene and polystyrene beads as described in (iii) above were soaked in Coating Solution B for about 2 minutes, removed from the Coating Solution, and were dried at ambient temperature for about 10 minutes. The beads were then returned to the Coating Solution B for about 1 minute, removed, and dried for an additional 10 minutes. Finally, the twice-coated beads were returned to Coating Solution B for about 1 minute, removed from the solution, and were dried at ambient room temperature for about 30 minutes.

Example 2

Tissue Necrosis With $AgNO_3$ Bearing Beads

Silver nitrate bearing beads prepared in Example 1 were placed on the surface of beef muscle tissue (fillet mignon). Beads without a silver nitrate coating were also placed on the tissue as negative controls, as was a crystal of pure silver nitrate (about 1 mm diameter by 3 mm length; as a positive control).

The surface of the tissue under each bead was observed at about 5 minute intervals for a total of about 15 to about 20 minutes. The degree of necrosis of the tissue under each bead was noted at each observation. The degree of necrosis was rated as follows:

slight visible pitting of the tissue surface (+); moderate pitting of tissue surface with slight blackening of the tissue (++); significant pitting with moderate blackening of the tissue (+++); severe pitting with complete blackening of the tissue (++++); and severe pitting with complete blackening of the tissue, spreading beyond the point of contact (+++++).

TABLE 1

Tissue Necrosis

| Bead Batch | Time (Minutes) | | | |
| --- | --- | --- | --- | --- |
| | 5 | 10 | 15 | 20 |
| AgNO$_3$ Crystal | +++ | ++++ | +++++ | N/A |
| PP Control | — | — | — | — |
| PS Control | — | — | — | — |
| Smooth Surface | | | | |
| PP (i) | + | N/A | ++ | ++$^a$ |
| PS (i) | + | N/A | ++ | ++$^b$ |
| PP (ii) | + | ++ | +++ | N/A$^c$ |
| PS (ii) | ++ | +++ | ++++ | N/A$^a$ |
| Rough Surface | | | | |
| PP (iii) | ++ | +++ | ++++ | N/A$^a$ |
| PS (iii) | ++ | +++ | ++++ | N/A$^a$ |
| PP (iv) | + | + | ++ | N/A$^a$ |
| PS (iv) | + | ++ | +++ | N/A$^a$ |

— = no observed necrosis; PP = polypropylene; PS = polystyrene
$^a$= bead penetrated the tissue to a depth of about ½ the diameter of the bead
$^b$= bead penetrated the tissue to a depth of about ¼ of the diameter of the bead
$^c$= bead penetrated the tissue to a depth of about ⅓ the diameter of the bead
N/A = not ascertained The degree of tissue necrosis observed for each bead type is recorded in Table 1. The data in Table 1 indicate that the silver nitrate coated beads as described herein provide an effective vehicle for delivering a tissue necrosing amount of silver nitrate to mammalian tissue.

Example 3

Tissue Necrosis With Acylonitrile-Butadiene-Styrene Beads

Two acrylonitrile-butadiene-styrene (ABS) beads (4 mm outside diameter) coated with a mixture of silver nitrate and potassium nitrate (50 mg total; AgNO$_3$:KNO$_3$ weight ratio 95:5) were inserted into beef muscle tissue (filet mignon). The beef muscle tissue was pre-heated to 37° C. in a warm water bath and then exposed to the coated beads for 20 minutes while at 37° C. and ambient pressure. The beads were held in direct contact with the beef muscle tissue during this time period so as to simulate the conditions in the uterine cavity. The two coated beads in the been muscle tissue were spaced about 10 millimeters apart.

Figure 3:
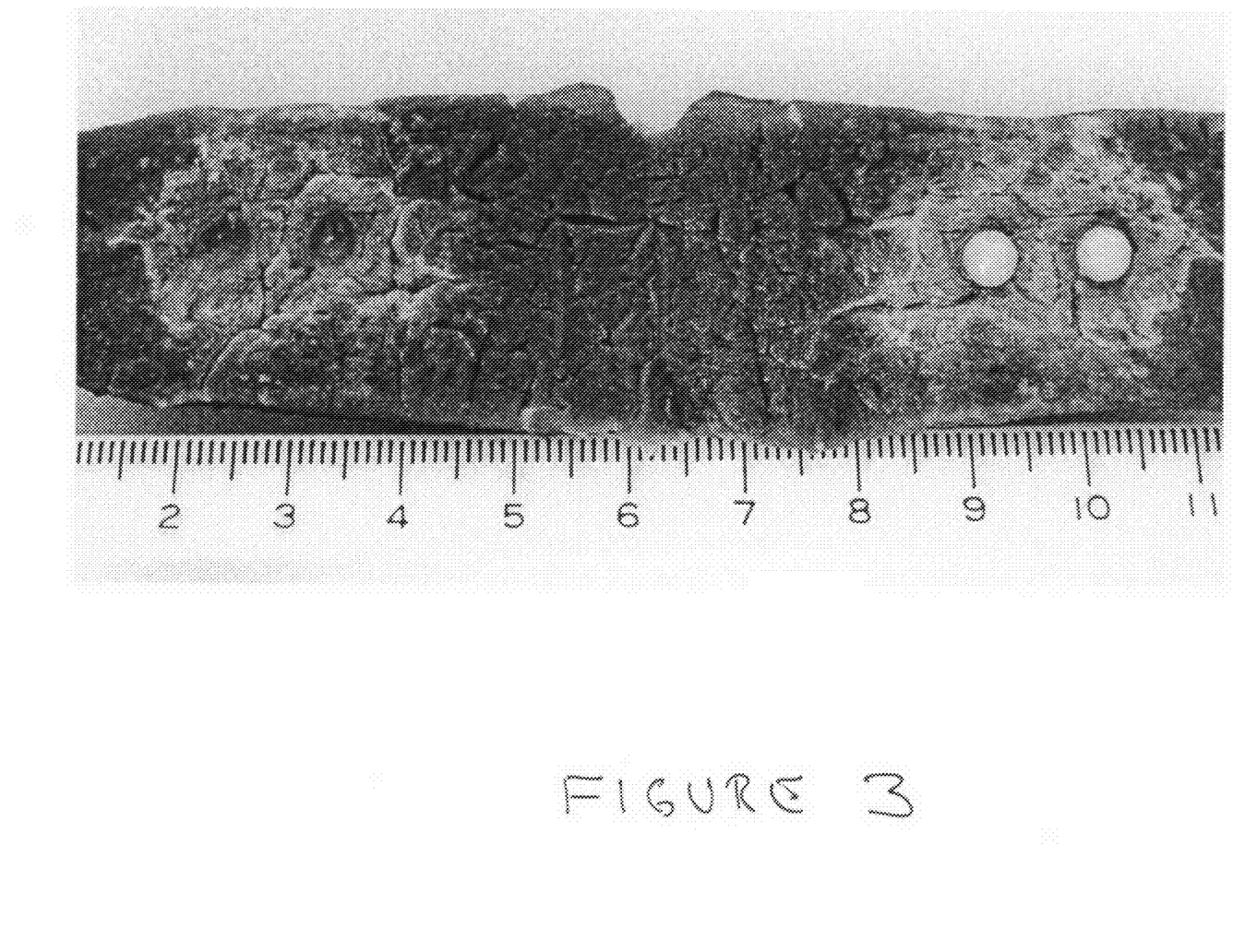
FIG. 3 is a photograph of a section of beef muscle tissue showing the positioning of two silver nitrate-bearing beads thereon and a surrounding region of necrosis.

After 20 minutes the beef muscle tissue was sliced open so as to reveal tissue that had been in contact with the AgNO$_3$ bearing surface of the ABS beads. The degree of achieved necrosis is shown in FIG. 3. The radius of necrosis (light gray region) around each bead was measured to be about 10 mm, and extended over the entire distance between the two beads. Also noted were some white regions believed to be silver chloride precipitate.

The so treated beef muscle tissue specimen was then washed with an aliquot of physiologic saline (10 ml; 0.9 w/v % of sodium chloride in one liter of water) to neutralize silver ions (Ag$^+$) present, and to precipitate as silver chloride (AgCl). Appearance of the specimen after neutralization is shown in FIG. 4.

The light gray regions seen in FIG. 3 were observed to be covered with a white precipitate. This indicated that some of the silver ions released from the beads had not as yet diffused into the beef muscle tissue.

Figure 4:
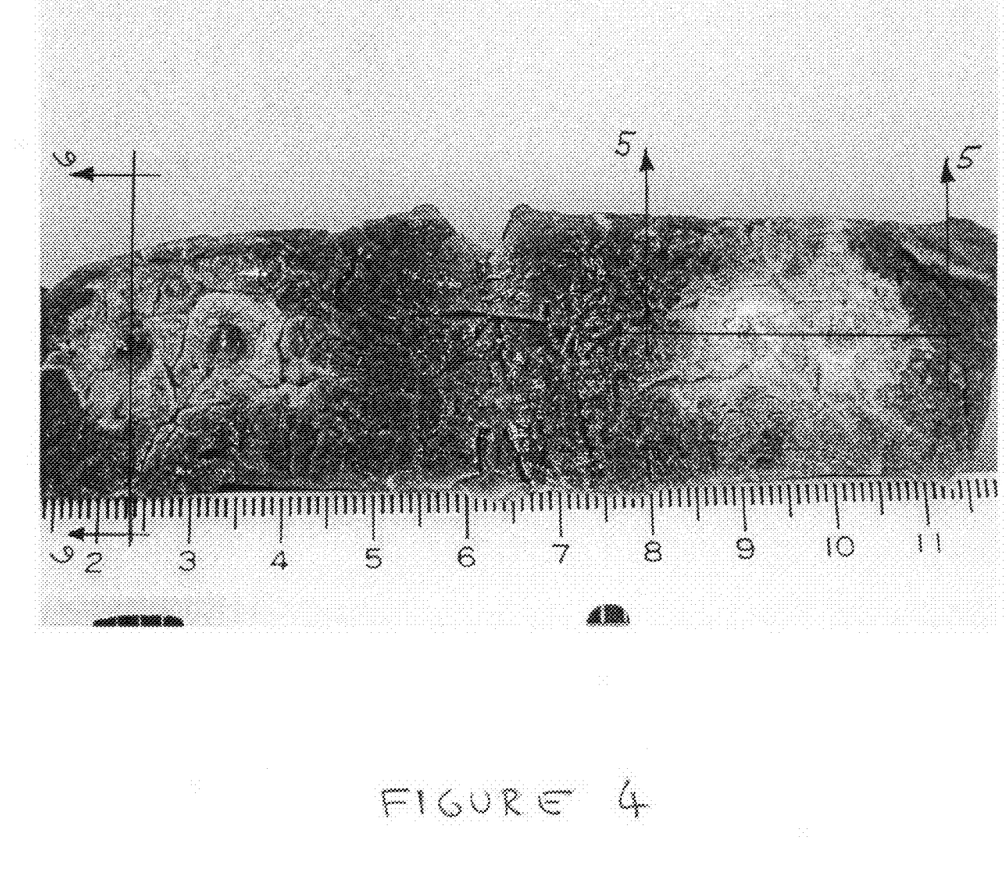
FIG. 4 is a photograph of the same section of beef muscle tissue as that shown in FIG. 3 but after neutralization with physiologic saline after the beads have been removed.
Figure 5:
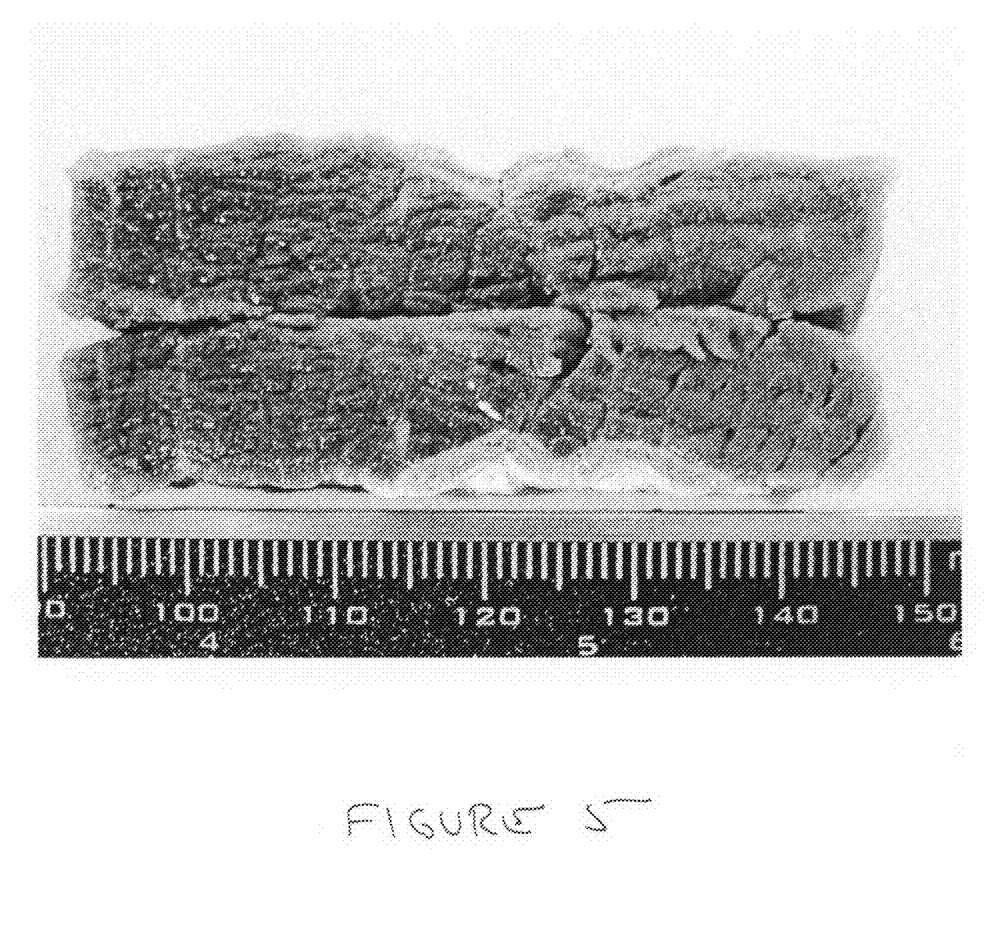
FIG. 5 is a section of the beef muscle tissue taken along plane 5-5 in FIG. 4.

To evaluate further the extent of necrosis by the two silver nitrate bearing beads, the specimen was sectioned along plane 5-5 in FIG. 4, i.e., across the midline of the indentations left by the beads, and then folded back unto itself. The appearance of this section is shown in FIG. 5. The depth of necrosis was measured to be about 3 mm. The necrosed portion was observed to be harder than the surrounding portions without necrosis, indicating a possible tissue fixation in addition to the tissue oxidation by the silver nitrate.

Figure 6:
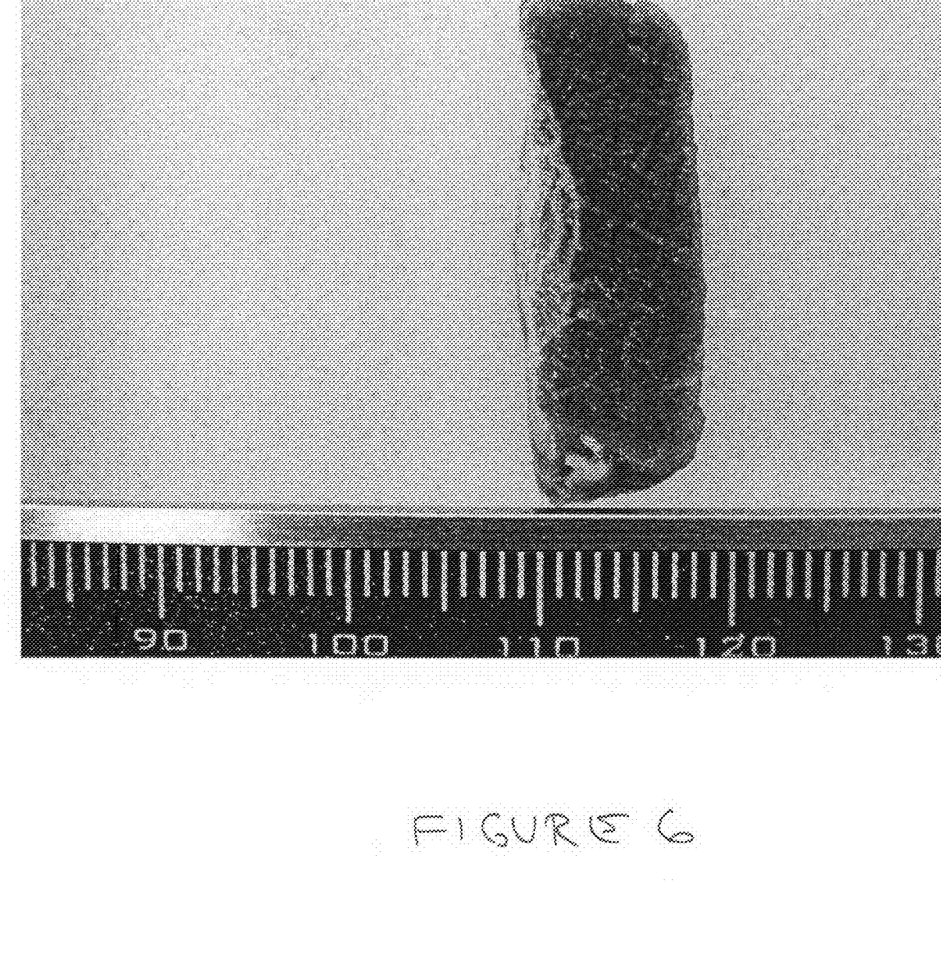
FIG. 6 is a section of the beef muscle tissue taken along plane 6-6 in FIG. 4.

Thereafter, the specimen shown in FIG. 5 was sectioned at a right angle to that shown in FIG. 5 and as indicated in FIG. 4 by plane 6-6. The appearance of this particular section is shown in FIG. 6. The necrosed region is substantially the same as that seen in FIG. 5 and indicates that silver nitrate had been diffusing into the tissue from the coated beads at substantially the same rate and to substantially the same depth around the bead.

The foregoing description is to be taken as illustrative, but not limiting. Still other variants within the spirit and scope of the present invention, including other uses for silver nitrate bearing beads, will readily present themselves to those skilled in the art.

I claim:

1. A method of treating menorrhagia comprising the steps of:
    administering to the uterine cavity of a patient suffering from menorrhagia a plurality of physiologically inert beads bearing a tissue necrosing amount of at least 20 mg or about 20 mg of silver nitrate as a solid silver ion source; said beads having an average diameter in the range of about 1 to about 6 millimeters;
    massaging the uterus to distribute the beads therein and maintaining the beads in contact with the endometrial lining of the uterus for a time sufficient to necrose the endometrial tissue;
    flushing the uterine cavity with a saline solution to neutralize any silver ions present in the uterine cavity; and
    recovering the beads from the patient's uterus.

2. The method in accordance with claim 1 wherein silver ions are administered in an amount in the range of about 25 mg/cue to about 150 mg/cm$^2$ of endometrium.

3. The method in accordance with claim 1 wherein silver ions are administered in an amount in the range of about 50 mg/cm$^2$ to about 100 mg/cm$^2$ of endometrium.

* * * * *

UNITED STATES PATENT AND TRADEMARK OFFICE
CERTIFICATE OF CORRECTION

PATENT NO. : 7,875,297 B2  
APPLICATION NO. : 12/231340  
DATED : January 25, 2011  
INVENTOR(S) : Robert S. Neuwirth Page 1 of 1

It is certified that error appears in the above-identified patent and that said Letters Patent is hereby corrected as shown below:

Column 7,
Line 5, "(+++++)" should be -- (++++) --.

Column 8,
Line 54, "mg/cue" should be -- mg/cm$^2$ --.

Signed and Sealed this
Fifth Day of July, 2011

David J. Kappos
*Director of the United States Patent and Trademark Office*